United States Patent
Pollack

(10) Patent No.: US 7,391,433 B2
(45) Date of Patent: Jun. 24, 2008

(54) MONITORING SYSTEM FOR HOSTILE ENVIRONMENT

(75) Inventor: Michael J. Pollack, Montgomeryville, PA (US)

(73) Assignee: Pollack Laboratories, Inc., Montgomeryville, PA (US)

( * ) Notice: Subject to any disclaimer, the term of this patent is extended or adjusted under 35 U.S.C. 154(b) by 651 days.

(21) Appl. No.: 10/058,658

(22) Filed: Jan. 28, 2002

(65) Prior Publication Data

US 2002/0101508 A1   Aug. 1, 2002

Related U.S. Application Data

(60) Provisional application No. 60/264,975, filed on Jan. 30, 2001.

(51) Int. Cl.
   *H04N 7/18* (2006.01)
(52) U.S. Cl. .......................... 348/85; 348/82
(58) Field of Classification Search ............... 73/54.01; 340/627; 348/45, 65, 70, 71, 82–85; 356/241.1, 356/241.4, 241.5; 374/121; 385/116; 600/109, 600/114, 160; 427/237; *H04N 7/18*
   See application file for complete search history.

(56) References Cited

U.S. PATENT DOCUMENTS

| | | | |
|---|---|---|---|
| 3,778,170 A | 12/1973 | Howell et al. | |
| 4,485,398 A | 11/1984 | Chapin, Jr. et al. | |
| 4,540,258 A * | 9/1985 | Chiodo | 600/109 |
| 4,591,794 A * | 5/1986 | Shattuck et al. | 340/627 |
| 5,048,956 A | 9/1991 | Sakamoto et al. | |
| 5,182,791 A | 1/1993 | Pollack | |
| 5,604,532 A | 2/1997 | Tillmanns | |
| 5,733,246 A | 3/1998 | Forkey | |
| 5,893,643 A * | 4/1999 | Kumar et al. | 374/121 |
| 5,956,077 A | 9/1999 | Qureshi et al. | |
| 5,993,902 A * | 11/1999 | Heid | 427/237 |
| 6,111,599 A * | 8/2000 | Nance et al. | 348/82 |
| 6,121,999 A | 9/2000 | Schaack | |
| 2002/0116987 A1 * | 8/2002 | Braithwaite et al. | 73/54.01 |

FOREIGN PATENT DOCUMENTS

GB   1042179   9/1966

* cited by examiner

Primary Examiner—Andy S Rao
(74) Attorney, Agent, or Firm—Howson & Howson LLP

(57) ABSTRACT

A monitoring system for monitoring a parameter of a hostile environment is provided within the interior of a sealed chamber. The chamber has a wall and an access port extending through the wall to the chamber exterior. The monitoring system includes a flexible, generally tubular, elongated housing having a distal end, a proximal end and a interior. The housing is made of a non-porous, corrosive resistant material. The distal end of the housing includes a sealed window and a sensor, which may be a borescope or camera, for sensing a parameter or for capturing an image within the hostile environment. The proximal end of the housing is sealingly secured to the chamber wall at the port so that the interior of the housing is accessible through the port. The interior of the housing includes a transmission media for transmitting an output signal of the sensor from the distal end of the housing to the proximal end of the housing and through the port. A monitor located outside of the chamber and connected to the transmission media receives and displays a representation of the sensor signal.

29 Claims, 3 Drawing Sheets

MONITORING SYSTEM FOR HOSTILE ENVIRONMENT

CROSS-REFERENCE TO RELATED APPLICATIONS

This application claims the benefit of U.S. Provisional Patent Application No. 60/264,975, filed Jan. 30, 2001 and entitled, "Optical Monitoring System" the entire subject matter of which is hereby incorporated herein by reference.

BACKGROUND OF THE INVENTION

The present invention relates generally to a monitoring system and, more particularly, to a monitoring system for monitoring or measuring one or more parameters, performing visual inspections or otherwise obtaining information from within a harsh or hostile environment such as within the interior of a sealed semiconductor wafer processing chamber.

There are many situations in which it is desirable to have the ability to measure or monitor one or more parameters or make visual inspections within a harsh or hostile environment. For example, it is desirable to have the ability to monitor one or more parameters, such as temperature and pressure, within the environment of a semiconductor wafer processing chamber. The environment within such a semiconductor wafer processing chamber, particularly during the processing of semiconductor wafers, includes high vacuum pressures. The use of existing, standard, unprotected monitoring equipment and/or techniques within such a semiconductor wafer processing chamber or any other such harsh or hostile environment is ineffective because most existing monitoring equipment is simply not constructed to withstand the severe pressures encountered within such a semiconductor wafer processing chamber and/or the severe temperatures, pressures and other environmental factors present in other such harsh or hostile environments. The present invention overcomes the problems of the prior art by providing a flexible, generally tubular elongated protective housing made of a non-porous, hermetically sealed, corrosive resistant material for containing the sensitive measuring and/or monitoring equipment employed for measuring or monitoring one or more parameters within a semiconductor wafer processing chamber or other such harsh or hostile environment. The present invention is particularly useful in calibration, inspection and maintenance within a semiconductor wafer processing chamber.

BRIEF SUMMARY OF THE INVENTION

Briefly stated, the present invention comprises, in one embodiment, a monitoring system for monitoring a parameter of a hostile environment within the interior of a sealed chamber. The chamber has a wall with an access port extending through the wall to the chamber exterior. The monitoring system comprises a flexible, generally tubular, elongated housing having a distal end, a proximal end and an interior. The housing is made of a non-porous, hermetically sealed, corrosive resistant material. The distal end of the housing contains a sealed window and a sensor for sensing a parameter of the hostile environment through the window. The proximal end of the housing is sealingly secured to the chamber wall at the access port so that the interior of the housing is accessible through the port. The interior of the housing includes a transmission media for transmitting an output signal of the sensor from the distal end of the housing to the proximal end of the housing and through the port. A monitor is located outside of the chamber and is connected to the transmission media for receiving the sensor signal and displaying a representation of the sensor signal.

In another embodiment, the present invention comprises an optical monitoring system for transmitting images from a hostile environment within the interior of a sealed chamber to the chamber exterior. The chamber has a wall and an access port extending through the wall. The monitoring system comprises a flexible, generally tubular, elongated housing having a distal end, a proximal end and an interior. The housing is made of a non-porous, hermetically sealed, corrosive resistant material. The distal end of the housing includes a sealed window and the proximal end of the housing is sealingly secured to the chamber wall at the access port so that the interior of the housing is accessible through the port. The interior of the housing includes a transmission media for transmitting images of the interior of the chamber obtained through the window from the distal end of the housing to the proximal end of the housing and through the port. A monitor is located outside of the chamber and is connected to the transmission media for receiving and displaying the images of the interior of the chamber.

In yet another embodiment, the present invention comprises an optical monitoring system for transmitting images from a hostile environment within the interior of a sealed chamber to the chamber exterior. The chamber has a wall with an access port extending through the wall. The monitoring system comprises a flexible, generally tubular, elongated housing having a distal end, a proximal end and an interior. The housing is made of a non-porous, hermetically sealed, corrosive resistant material. The distal end of the housing includes a sealed window and the proximal end of the housing is sealingly secured to the chamber wall at the access port so that the interior of the housing is accessible through the port. A camera is positioned within the distal end of the housing to record images of the interior of the chamber through the window. The interior of the housing includes a transmission media for transmitting the images of the interior of the chamber as recorded by the camera from the distal end of the housing to the proximal end of the housing through and the port. A monitor is located outside of the chamber and is connected to the transmission media for receiving and displaying the recorded images of the interior of the chamber.

In a further embodiment, the present invention comprises an optical monitoring system for transmitting images from a hostile environment within the interior of a sealed chamber to the chamber exterior. The chamber has a wall with an access port extending through the wall. The monitoring system comprises a flexible, generally tubular, elongated housing having a distal end, a proximal end and an interior. The housing is made of a non-porous hermetically sealed, corrosive resistant material. The distal end of the housing includes a sealed window and the proximal end of the housing is sealingly secured to the chamber wall at the access port so that the interior of the housing is accessible through the port. The interior of the housing includes a borescope for transmitting images of the interior of the chamber obtained through the window from the distal end of the housing to the proximal end of the housing and through the port. A monitor is located outside of the chamber and is connected to the borescope for receiving and displaying the images of the interior of the chamber.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
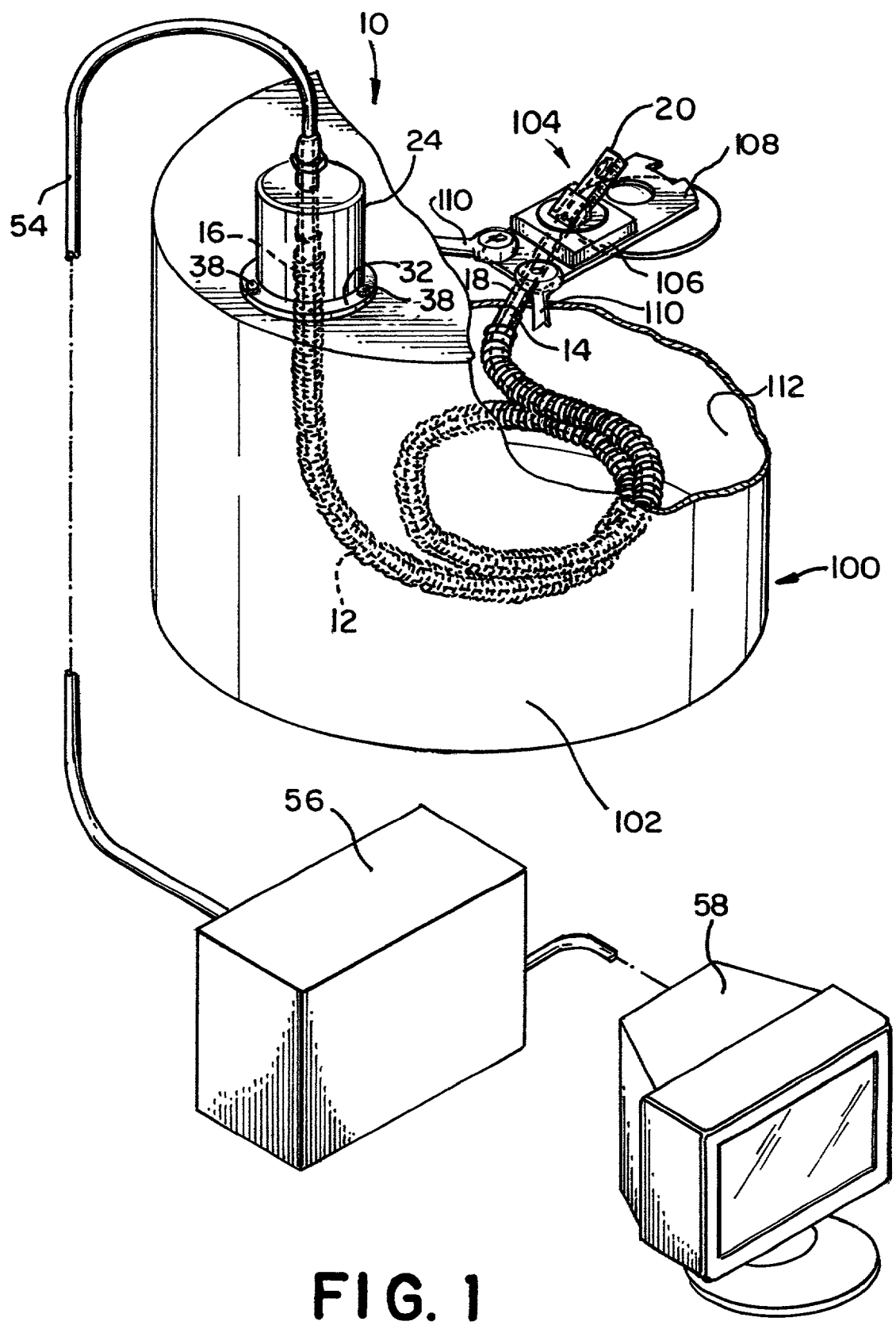
FIG. 1 is a diagrammatic perspective view, partially broken away, of a semiconductor wafer processing chamber, including a monitoring system in accordance with a preferred embodiment of the present invention.

Referring to the drawings, wherein like numerals are used to designate like components throughout the several figures, there is shown in FIG. 1, a diagrammatic representation of a portion of a semiconductor wafer processing chamber 100 within which is positioned a monitoring system 10 in accordance with a first preferred embodiment of the present invention. The semiconductor wafer processing chamber 100, which in the present configuration is shown as being generally cylindrical, includes a wall 102 comprised of a generally vertically extending, generally cylindrical portion and generally circular upper and lower portions which together function to establish the generally sealed chamber 100. The materials employed and the methods employed for forming the chamber 100 are well known to those of ordinary skill in the art and are not necessary for a complete understanding of the present invention. Contained within the chamber 100 are the equipment and components (not shown) necessary for establishing the environment required for processing semiconductor wafers. Such equipment and components are also well known to those of ordinary skill in the art and further details regarding the structure and operation of such equipment and components are not necessary for a complete understanding of the present invention. One such component which is contained within the chamber 100 is a robot assembly 104, which is primarily employed for the purpose of transferring semiconductor wafers into and out of the chamber 100 through a suitable slot-like sealed doorway (not shown) and for moving the wafers to various processing stations (not shown) within the chamber 100. The robot assembly 104 is comprised of a moveable base member 106, a wafer holding assembly 108 and a pair of supporting linkage members 110, which are employed for moving the remainder of the robot assembly 104 to the chamber doorway and to various locations within the chamber 100 to facilitate processing of semiconductor wafers. The robot assembly 104 is of a type well known to those of ordinary skill in the semiconductor wafer processing art. Further details concerning the structure and operation of the robot assembly 104 are not necessary for a complete understanding of the present invention.

The foregoing description relates to a semiconductor wafer processing chamber 100 of the type diagrammatically illustrated by FIG. 1 and well known to those of ordinary skill in the semiconductor wafer processing art. Such chambers are commercially available from well known manufacturers, including Applied Materials, Inc. Further details regarding the structure and operation of the chamber 100 are available from the manufacturers and a variety of publicly available sources and are not necessary for a complete understanding of the present invention. As is also understood by those of ordinary skill in the art, during a semiconductor wafer processing operation, the interior 112 of a semiconductor wafer processing chamber 100 of the type described and shown is at temperatures in the range of 25° C. ±10° and is subject to vacuum pressures in the range of $10^{-7}$ Torr which functions to create a harsh or hostile environment, which effectively precludes the use of standard, unprotected sensing or monitoring equipment and techniques, including a video camera or other viewing equipment. The inability to use such sensing equipment and techniques and/or a video camera or other viewing equipment within such a semiconductor wafer processing chamber 100 makes it much more difficult to fully know the values of certain parameters within the chamber which are needed to better control the processing of semiconductor wafers therein. The present invention overcomes the difficulties associated with the prior art by providing a system for measuring or monitoring one or more parameters or obtaining visual images from within a hostile or harsh environment such as the environment present within a semiconductor wafer processing chamber 100 during the processing of semiconductors.

A first embodiment of the present invention as illustrated in FIGS. 1-4 comprises an optical monitoring system 10 for transmitting images from the hostile environment within the interior 112 of the sealed semiconductor processing chamber 100 to the chamber exterior. In the present embodiment, the optical monitoring system 10 is comprised of a flexible, generally tubular elongated protective housing 12 having a first or distal end 14 and a second or proximal end 16. The protective housing 12, which is used to protect a sensor, camera or the like from the harsh environment within the chamber 100, is made of a non-porous, hermetically sealed, corrosive resistant material. As shown in FIG. 1, the housing 12 comprises a shroud or sheath which is preferably formed of a stainless steel bellows, thereby making the housing 12 generally flexible for movement of at least the distal end 14 about the chamber 100 in a manner which will hereinafter be described. The bellows is preferably of the helical type but could be of the discrete ring type or some other type. It will be appreciated by those of ordinary skill in the art that other materials may alternatively be employed, including other metals or metal alloys, polymeric materials, such as polypropylene, composite materials and the like. Accordingly, the particular material employed for making the protective housing 12 should not be considered to be a limitation on the present invention. In addition, the protective housing 12 need not be in the form of a bellows, as long as it is sufficiently flexible and gas tight. Preferably, the thickness of the protective housing 12 is sufficient to provide the needed protection in the particular environment within which the monitoring system 10 is employed. In the case of a semiconductor wafer processing chamber 100, the thickness of the preferred stainless steel bellows is in the range of 0.010 to 0.015 inch. In the present embodiment, the bellows has an outside diameter or about ⅝ inch and a length of about three feet. However, the dimensions of the bellows may vary depending on the application.

Figure 2:
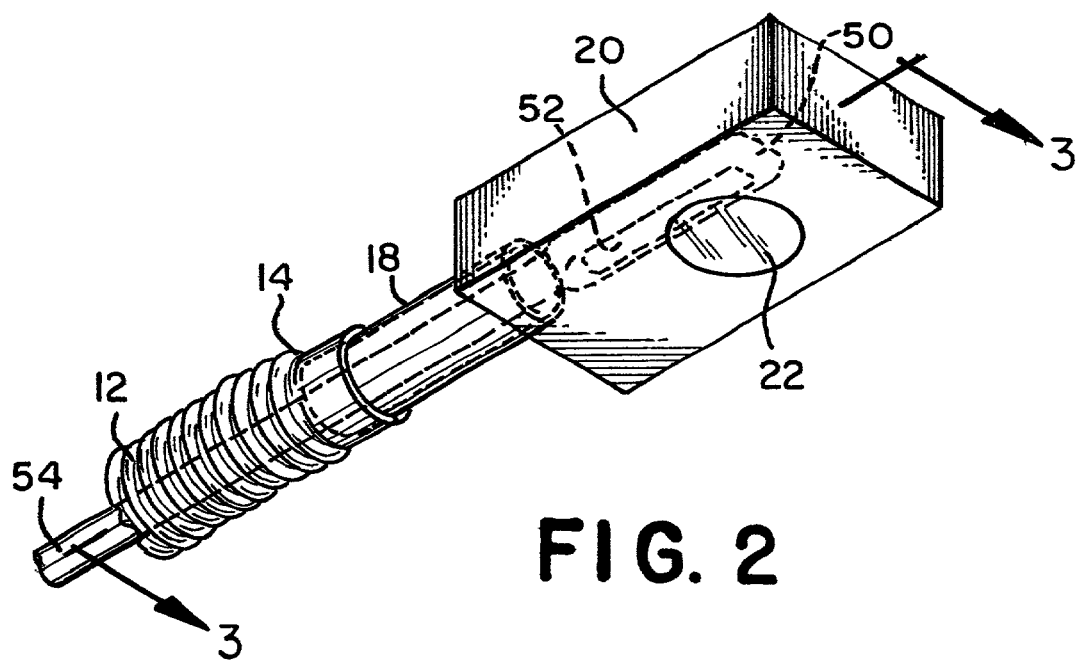
FIG. 2 is a greatly enlarged perspective view of the distal end portion of an elongated housing of the monitoring system of FIG. 1.
Figure 3:
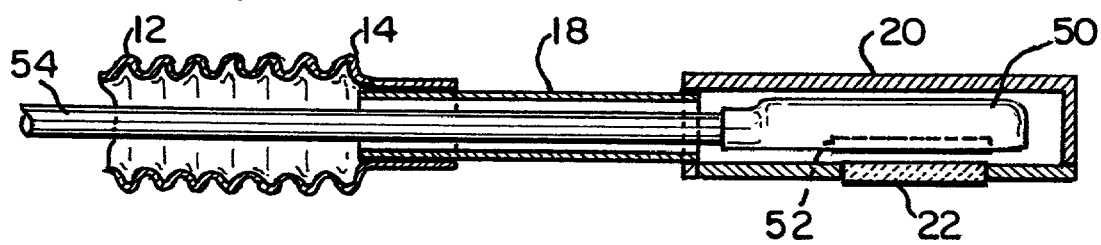
FIG. 3 is a cross-sectional view of the distal end of the housing taken along line 3-3 of FIG. 2.

As best shown in FIGS. 2 and 3, the housing 12 further includes a generally tubular member 18 which extends outwardly from the distal end 14 of the bellows portion. A sensor housing 20 is secured to the distal end of the tubular member 18. Both the tubular member 18 and the sensor housing 20 are preferably made of a high strength, non-porous, hermetically sealed, corrosive resistant material, such as stainless steel. However, other materials, including polymeric materials, may alternatively be employed. Preferably, the proximal end of the tubular member 18 is secured to the distal end 14 of the bellows portion of the housing 12 using brazing, welding, an adhesive or any other suitable securing means which provides a gas tight connection. Similarly, the sensor housing 20 is secured to the distal end of the tubular member 18 using brazing, welding, an adhesive or any other suitable method providing a gas tight connection.

The sensor housing 20 is generally in the form of a parallelepiped and includes a sealed window 22 on at least one surface. The window 22 is generally flat and is formed of a material which is resistant to the hostile environment within the chamber 100 but which also has high light transmission, particularly in the infrared, visible and ultraviolet ranges. Preferably, the window 22 is formed from a single crystal synthetic sapphire but it could be formed of glass, quartz, a polymeric material or any other light transmissive material which is resistant to the environment within the chamber 100. In the preferred embodiment, the window 22 is generally circular, is formed of synthetic sapphire and is secured by brazing within a suitably sized generally circular opening within one surface of the sensor housing 20. If desired, some other method may be employed for securing the window 22 within the opening of the sensor housing 20 including using fusion, an adhesive, or any other suitable securing method or device which provides a gas tight connection. In this manner, a hermetically sealed protective environment is established within the housing 12 as a result of the materials employed in making the bellows portion of the housing 12, tubular member 18, sensor housing 20 and window 22 and as a result of having all such components being secured together with gas tight connections and hermetically sealed as described above. In the present embodiment, the sensor housing 20 is generally in the shape of a flat parallelepiped. However, it will be appreciated by those of ordinary skill in the art that the sensor housing 20 could have some other shape, for example, it could be cylindrical, or of any other suitable shape. In addition, in the present embodiment, the window 22 is generally circular. It will be apparent to those of ordinary skill in the art that the window 22 could be square, rectangular or of any other suitable shape. Also, in the presently preferred embodiment, the generally rigid tubular member 18 extends between the distal end 14 of the bellows portion of the housing 12 and the sensor housing 20. It will be appreciated by those of ordinary skill in the art that, if desired, the sensor housing 20 could be secured directly to the distal end 14 of the bellows portion of the protective housing 12.

Figure 4:
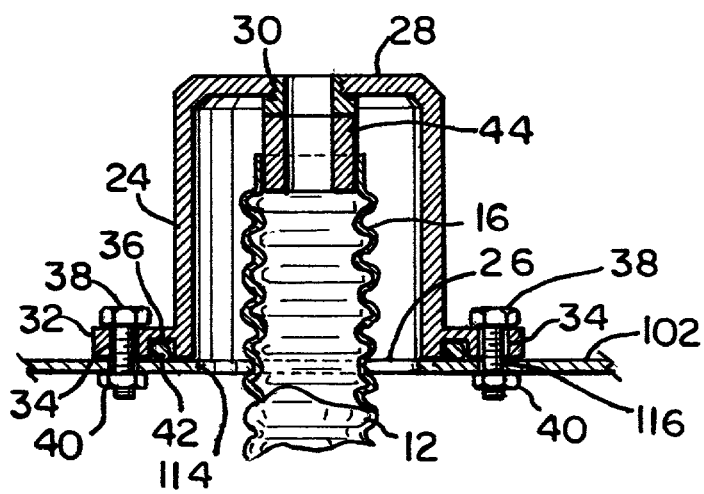
FIG. 4 is a greatly enlarged cross-sectional view of the port mounting housing portion of the monitoring system of FIG. 1.

As best shown in FIG. 4, the chamber 100 includes an opening or access port 114 extending the through the wall 102 between the exterior and interior 112 thereof. In the illustrated embodiment, the access port 114 is generally circular and is located on the upper or top surface of the chamber wall 102. It will be appreciated by those of ordinary skill in the art that the access port 114 could extend through the chamber wall 102 at any other suitable location. In the present embodiment, the access port 114 is generally circular and has a predetermined diameter which is at least slightly greater than the outer dimension of the bellows portion of the protective housing 12. It will be appreciated by those of ordinary skill in the art that the size and shape of the access port 114 may vary from the size and shape as shown and described. Thus, it should be clearly understood that the size, shape and location of the access port 114 should not be considered to be a limitation upon the present invention. In addition, while in the present embodiment, a single access port 114 is shown, It will be appreciated by those of ordinary skill in the art that multiple access ports (not shown) could be positioned at multiple locations along the chamber wall 102.

The optical monitoring system 10 further includes a port housing 24 positioned on the exterior surface of the chamber wall 102 to generally cover and enclose the access port 114. As best shown in FIGS. 1 and 4, the port housing 24 is generally cylindrically shaped with a diameter at least slightly greater then the diameter of the access port 114 and with a generally open first end 26 and a second end 28, which is generally closed with the exception of a generally circular hole or opening 30 extending generally through the radial center thereof. The first end 26 of the port housing 24 includes a generally, radially outwardly extending annular flange 32, which is employed for engaging and securing the port housing 24 to the exterior surface of the chamber wall 102. The annular flange 32 includes a plurality of generally radially spaced, generally circular openings 34 extending therethrough and a generally annular sealing groove 36 on the surface which faces the exterior surface of the chamber wall 102. The chamber wall 102 includes a plurality of openings 116 extending therethrough and surrounding the access port 114, the chamber wall openings 116 being circumferentially spaced in a generally circular pattern which corresponds to the pattern of the openings 34 extending through the annular flange 32. In this manner, when the port housing 24 is placed on the exterior surface of the chamber wall 102 over the access port 114 with the openings 34 on the annular flange 32 aligned with the openings 116 of the chamber wall 102, a plurality of fasteners, such as bolts 38 and corresponding nuts 40 may be employed for securing the port housing 24 to the chamber wall 102. Prior to securing the port housing 24 to the chamber wall 102, an annular sealing ring 42, such as an elastomeric O-ring, is installed within the sealing groove 36. In this manner, the port housing 24 may be hermetically sealed to the chamber wall 102 surrounding the access port 114. It will be appreciated by those of ordinary skill in the art that the port housing 24 may be sealingly secured to the exterior of the chamber wall 102 by clamping, the use of an adhesive or any other manner known to those of ordinary skill in the art to provide a hermetic seal between the port housing 24 and the chamber wall 102. Preferably, the port housing 24 is made of a non-porous, corrosive resistant high strength material. In the present embodiment, the port housing 24 is made of stainless steel. However, other materials, including other metals and metal alloys, polymeric materials, composite materials or the like may alternatively be employed for forming the port housing 24. In addition, the port housing 24 could be of some other shape, if desired.

A generally tubular coupling member 44 extends through the opening 30 of the second end 28 of the port housing 24 and into the port housing interior. The first or upper end of the coupling member 44 sealingly engages the port housing opening 30 with a gas tight, but rotatable fit. The proximal end 16 of the protective housing 12 is secure to the second or lower end of the coupling member 44. Preferably, the proximal housing end 16 is secured to the coupling member 44 using brazing, fusion, an adhesive or in some other manner well known to those of ordinary skill in the art to provide a permanent, gas tight connection therebetween. In this manner, the coupling member 44 and thus the housing 12, while supported within the port housing 24 may rotate with respect to the port housing opening 30 to facilitate movement of the protective housing 12 within the chamber 100 in a manner which will hereinafter be described. In an alternative embodiment, the coupling member 44 is permanently and non-rotatably secured within the port housing opening 30. If desired, an arrangement, other than the coupling member 44 may be employed for rotatably or non rotatably supporting the proximal end 16 of the housing 12 within the port housing 24 with a gas tight connection.

The optical monitoring system 10 as thus far described provides a hermetically sealed, safe environment for a sensor or other device which may be moved to various locations within the chamber 100 in a manner which will hereinafter be described. Thus, a complete sealed path is established from the exterior of the chamber 100 through the port housing opening 30, the coupling member 44 and the bellows portion, tubular member 18 and sensor housing 20 of the protective housing 12 so that sensors or other devices can be positioned within the sensor housing 20 inside of the chamber 100 without being exposed to the harsh environment within the chamber 100.

It will be appreciated by those of ordinary skill in the art that a variety of different sensors could be installed within the protected environment of the housing 12, as thus far described. Such sensors could include, for example, a temperature sensor, preferably of the infrared type commercially available from various manufacturers including Mikron of Northern New Jersey, a pressure sensor, preferably of the infrared type commercially from various manufacturers and an oxygen sensor, such as laser RAMAN sensor commercially available from various manufacturers, including Kaiser Optics of Ann Arbor, Mich., a spectrographic chemical analysis sensor commercially available from various manufacturers, including Custom Sensor of Wisconsin, a level sensor or the like. Any sensor or group of sensors which may be employed are preferably positioned within the sensor housing 20 proximate to the sealed window 22 for performing the requisite sensing task. A suitable transmission media, such as one or more electrical wires could extend from each such sensor and within the protective environment through the sensor housing 20, tubular member 18, flexible portion of the protective housing 12 and port housing 24 to the exterior of the chamber 100 where the proximal end of any such transmission media could be secured to a suitable electrical or electronic device, such as a display, computer, or the like for collecting, processing, analyzing, monitoring or displaying plots or other representations of the electrical signals received from the sensor.

In the preferred embodiment as illustrated by FIGS. 1-3, an optical sensor, such as a borescope 50, is employed. The borescope 50 may be of the flexible or rigid type, depending on the particular application. In the present embodiment, the borescope 50 is of the flexible lensed type and is commercially available from a variety of sources, including Olympus International of Mitchell Field, N.Y. As shown in phantom in FIGS. 1 and 2, the distal or viewing end of the borescope 50 extends into the sensor housing 20 with the viewing portion 52 of the borescope 50 generally aligned with and facing the sealed window 22. A light source (not shown) may also be incorporated within or may be secured to the borescope 50. In this manner, the borescope 50 may sense or obtain images of the interior of the chamber 100 through the window 22. The transmission media of the borescope 50, in the present embodiment, a coherent fiber optic bundle 54, extends from the viewing portion 52 within the sensor housing 22 through the tubular member 18, bellows portion of the protective housing 12 and port housing 24 and into a suitable control box 56 (shown schematically in FIG. 1). The control box 56 includes elements (such as, lenses and a camera) well known to those of ordinary skill in the art for converting optical images received from the borescope 50 into electrical signals which are then passed along a wire or cable to a suitable video monitor 58 for display to a user.

In an alternate embodiment, instead of a borescope 50, a camera could be employed. The camera may be of the video type well known to those of ordinary skill in the art and may be of the infrared, visible spectrum or ultra violet type. The camera could be a UGA, an SVGA, an XGA or MEGA pixel camera and the resolution of the camera could vary depending upon the application. Preferably, the camera is of the complimentary metal-oxide semiconductor (CMOS) type, but it could be a change coupled device (CCD) or any other type. In the present embodiment, a CCD camera available from Olympus International of Mitchell Field, N.Y. is employed. Preferably, the camera includes a light source to facilitate capturing images in low light conditions. Signals from the video camera are transmitted by the transmission media, in the form of one or more electrical wires or cables which extend from the sensor housing 20, through the tubular member 18, bellows portion of the protective housing 12 and port housing 24 and are connected to a suitable video monitor 58 for displaying to a user images obtained by the video camera through the sealed window 22. In this manner, conditions within the interior 112 of the chamber 100 may be viewed and monitored Regardless of whether the sensor is comprised of a borescope 50, video camera or some other sensor as described above, the distal end 14 of the protective housing 12, with or without the tubular member 18, is preferably secured to the base member 106 of the robot assembly 104, at least on temporary basis. In this manner, the robot assembly 104, in addition to performing its normal duties within the semiconductor wafer processing chamber 100, can be used for moving the sensor housing 20 with the sensor, borescope or camera therein to various locations within the chamber 100. The monitoring system 10 may thus be employed for monitoring conditions, as well as to provide optical viewing at various locations throughout the semiconductor wafer processing chamber 100. A suitable clamp (not shown) clip (not shown) or any other suitable fastening member or material may be employed for securing the tubular member 18 and/or sensor housing 20 to the base member 106 of the robot assembly 104. In the embodiment shown in FIG. 1 the sensor housing 20 extends upwardly, at an angle from the robot base member 106 for enhanced viewing.

Figure 5:
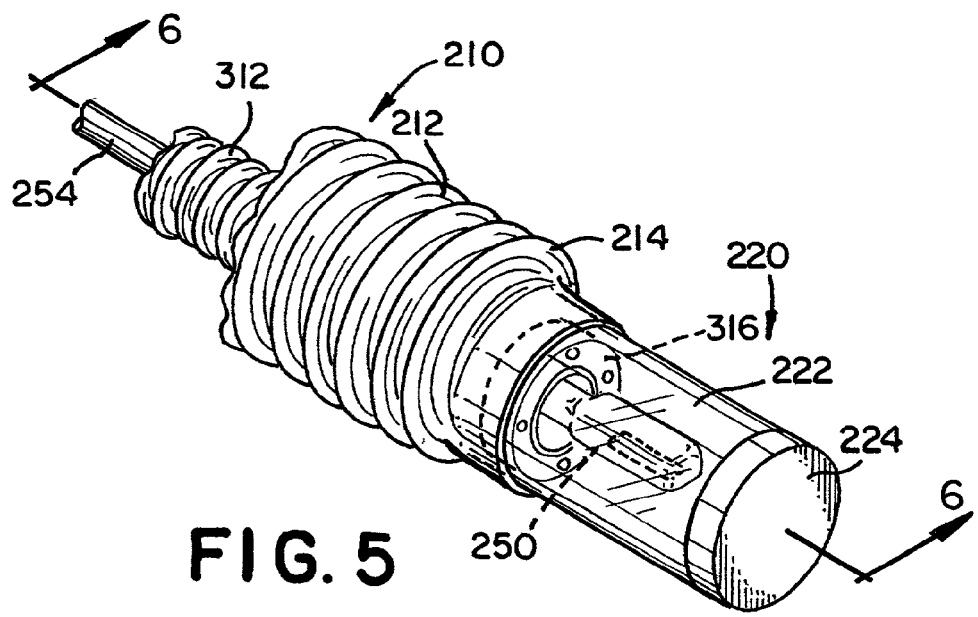
FIG. 5 is a greatly enlarged perspective view of the distal end portion of an elongated housing in accordance with an alternate embodiment of the present invention.
Figure 6:
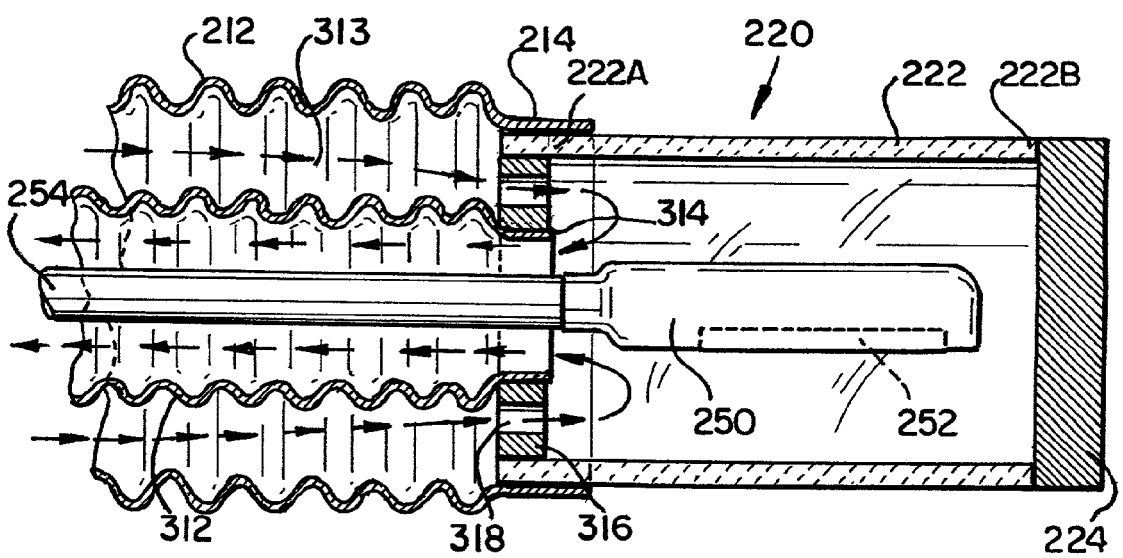
FIG. 6 is an enlarged cross-sectional view of a portion of the alternate embodiment taken along line 6-6 of FIG. 5.

Referring now to FIGS. 5 and 6, there is shown a monitoring system 210 in accordance with an alternate embodiment of the present invention. As with the above-described embodiment, the monitoring system 210 is comprised of a flexible, generally tubular elongated bellows-like portion of the protective housing 212, which is substantially the same as the protective housing 12 as described above. The bellows-like portion of the protective housing 212 has a first or distal end 214 which is secured to a sensor housing 220. However, unlike the sensor housing 20 of the above-described embodiment, the sensor housing 220 of the present embodiment is generally cylindrically shaped and is formed of a generally tubular, generally continuous window 222. The window 222 is preferably made of one of the same materials employed in making the window 22 of the above-described embodiment. A first or proximal end of the window 222A is secured to the distal end 214 of the bellows-like portion of the protective housing 212 in substantially the same manner as described above in connection with the first preferred embodiment to provide a gas tight seal therebetween. The second or distal end of the window 222B is enclosed by a cap member 224. Preferably, the cap member 224 is secured to the distal end 222B of the window 222 in the same manner as described above in connection with the first embodiment to provide a gas tight seal therebetween. By providing a sensor housing 220 formed of a generally continuous tubular window 222, a borescope 250 installed therein may be rotated 360° so that the optical window 252 of the borescope may capture images at virtually any desired angle or location. As with the above-described embodiment, images captured by the borescope 250 are transmitted out of the chamber 100 by a fiber optic bundle 254. Preferably, the end cap 224 is made of stainless steel or some other high strength metal, metal alloy or polymeric material.

As best shown in FIG. 6, the present embodiment includes additional components which may be employed for more particularly controlling the environment within the interior of the sensor housing 220. A second flexible, generally tubular elongated housing 312 is provided within the interior of the bellows-like portion of the primary protective housing 212 to create a generally annular space 313 therebetween. The inner housing 312 includes a distal end 314 which is secured to a plug member 316 in the annular space 313 at the proximal end 222A of the window 222. The plug member 316 which is generally annular and is preferably made of stainless steel or a polymeric material, includes a plurality of circumferentially spaced, generally circular openings 318 extending completely therethrough. In this manner, fluid, under pressure, may be provided from the proximal end of the protective housing 212 within the annular space 313. As shown by the arrows on FIG. 6, the fluid flows along and out of the annular space 313 through the plug member openings 318, into the sensor housing 220 and returns to the proximal end of the housing 212 within the inner housing 313. The fluid may be a cooling fluid, a heating fluid or some other fluid employed for controlling the environment within the interior of the protective housing 212 and particularly the sensor housing 220 where the sensor, camera, etc. is located. In addition to controlling the environment within the sensor housing 220, the fluid controls the environment within the rest of the protective housing 212 as it passes through the annular space 313. In one embodiment, the fluid flow is provided at approximately 20 lbs. per square inch at approximately 12 cubic ft. per hour. By controlling the environment within the interior of the protective housing 212 and particularly within the interior of the sensor housing 220, the monitoring system 210 is able to function to provide images and/or to monitor or measure parameters in more hostile environment. If desired, the fluid may be used to increase the pressure within the housing 12 to decrease the pressure differential between the interior and exterior of the housing 12.

In a further alternate embodiment (not shown), the sensor, or at least a distal end of the sensor extends through a sealed opening within the sensor housing 20 or 220 to provide direct access to the interior of the chamber 100.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An optical monitoring system for transmitting images from a hostile environment within the interior of a sealed chamber to the chamber exterior, the chamber having a wall and an access port extending through the wall, the monitoring system comprising:

a flexible, generally tubular, elongated, hermetically sealed housing having a distal end, a proximal end and an interior, the housing being made of a non-porous, corrosive resistant material, the distal end of the housing including a sealed window, the proximal end of the housing being rigidly secured to the chamber wall at the access port to form a hermetic seal between the proximal end of the housing and the chamber, the interior of the housing being accessible through the access port, the interior of the housing including a transmission media for transmitting images of the interior of the chamber obtained through the window from the distal end of the housing to the proximal end of the housing and through the access port; and a monitor located outside of the chamber and connected to the transmission media for receiving and displaying the images of the interior of the chamber.

2. The optical monitoring system recited in claim 1, wherein the housing comprises a flexible sheath formed of a stainless steel bellows.

3. The optical monitoring system recited in claim 1, wherein the housing comprises a flexible polymeric tube.

4. The optical monitoring system recited in claim 1, wherein the window is formed from a material selected from the group consisting of synthetic sapphire, glass, quartz and a polymeric material.

5. The optical monitoring system recited in claim 4, wherein the window is secured to the housing by a method selected from the group consisting of brazing, fusion and an adhesive.

6. The optical monitoring system recited in claim 1, wherein the housing includes a borescope having a viewing end which is aligned with the sealed window.

7. The optical monitoring system recited in claim 1, wherein the transmission media is comprised of a coherent fiber optic bundle.

8. The optical monitoring system recited in claim 1, wherein the interior of the housing is provided with a fluid under pressure to control the environment within the interior of the housing.

9. An optical monitoring system for transmitting images from a hostile environment within the interior of a sealed chamber to the chamber exterior, the chamber having a wall and an access port extending through the wall, the monitoring system comprising:

a flexible, generally tubular, elongated, hermetically sealed housing having a distal end, a proximal end and an interior, the housing being made of a non-porous, corrosive resistant material, the distal end of the housing including a sealed window and a camera positioned to record images of the interior of the chamber through the window, the proximal end of the housing being rigidly secured to the chamber wall at the access port to form a hermetic seal between the proximal end of the housing and the chamber, the interior of the housing being accessible through the access port, the interior of the housing including a transmission media for transmitting the images of the interior of the chamber recorded by the camera from the distal end of the housing to the proximal end of the housing and through the access port; and a monitor located outside of the chamber and connected to the transmission media for receiving and displaying the recorded images of the interior of the chamber.

10. The optical monitoring system as recited in clam 9, wherein the camera is a video camera.

11. The optical monitoring system as recited in claim 9, wherein the housing comprises a flexible sheath formed of a stainless steel bellows.

12. The optical monitoring system as recited in claim 9, wherein the housing comprises a flexible polymeric tube.

13. The optical monitoring system as recited in claim 9, wherein the window is formed from a material selected from the group consisting of synthetic sapphire, glass, quartz and a polymeric material.

14. The optical monitoring system as recited in claim 9, wherein the window is secured to the housing by a method selected from the group consisting of brazing, fusion and an adhesive.

15. The optical monitoring system as recited in claim 9, wherein the camera is an infrared camera.

16. The optical monitoring system as recited in claim 9, wherein the interior of the housing is provided with a fluid under pressure to control the environment within the interior of the housing.

17. An optical monitoring system for transmitting images from a hostile environment within the interior of a sealed chamber to the chamber exterior, the chamber having a wall and an access port extending through the wall, the monitoring system comprising:

a flexible, generally tubular, elongated, hermetically sealed housing having a distal end, a proximal end and an interior, the housing being made of a non-porous corrosive resistant material, the distal end of the housing including a sealed window, the proximal end of the housing being rigidly secured to the chamber wall at the access port to form a hermetic seal between the proximal end of the housing and the chamber, the interior of the housing being accessible through the access port, the interior of the housing including a flexible borescope for transmitting images of the interior of the chamber obtained through the window from the distal end of the housing to the proximal end of the housing and through the access port; and a monitor located outside of the chamber and connected to the borescope for receiving and displaying the images of the interior of the chamber.

18. The optical monitoring system as recited in claim 17, wherein the housing comprises a flexible sheath formed of a stainless steel bellows.

19. The optical monitoring system recited in claim 17, wherein the housing comprises a flexible polymeric tube.

20. The optical monitoring system as recited in claim 17, wherein the window is formed from a material selected from the group consisting of synthetic sapphire, glass, quartz and a polymeric material.

21. The optical monitoring system as recited in claim 17, wherein the window is secured to the housing by a method selected from the group consisting of brazing, fusion and an adhesive.

22. The optical monitoring system as recited in claim 17, wherein the interior of the housing is provided with a fluid under pressure to control the environment within the interior of the housing.

23. A monitoring system for monitoring a parameter of a hostile environment within the interior of a sealed chamber, the chamber having a wall and an access port extending through the wall to the chamber exterior, the monitoring system comprising:

a flexible, generally tubular, elongated, hermetically sealed housing having a distal end, a proximal end and an interior, the housing being made of a non-porous, corrosive resistant material, the distal end of the housing including a sealed window and a sensor for sensing a parameter of the hostile environment through the window, the proximal end of the housing being rigidly secured to the chamber wall at the access port to form a hermetic seal between the proximal end of the housing and the chamber, the interior of the housing being accessible through the access port, the interior of the housing including a transmission media for transmitting an output signal of the sensor from the distal end of the housing to the proximal end of the housing and through the access port; and an apparatus located outside of the chamber and connected to the transmission media for receiving and processing the sensor signal and displaying a representation of the sensor signal.

24. The optical monitoring system as recited in claim 23, wherein the sensor is selected from the group consisting of a temperature sensor, a pressure sensor, an oxygen sensor and a spectra graphic chemical analysis sensor.

25. The optical monitoring system as recited in claim 23, wherein the housing comprises a flexible sheath formed of a stainless steel bellows.

26. The optical monitoring system as recited in claim 23, wherein the housing comprises a flexible polymeric tube.

27. The optical monitoring system as recited in claim 23, wherein the window is formed from a material selected from the group consisting of synthetic sapphire, glass, quartz and a polymeric material.

28. The optical monitoring system as recited in claim 23, wherein the housing further includes a sealed window secured to the distal end of the housing by a method selected from the group consisting of brazing, fusion and an adhesive.

29. The optical monitoring system as recited in claim 23, wherein the interior of the housing is provided with a fluid under pressure to control the environment within the interior of the housing.

* * * * *